(12) United States Patent
Wanda

(10) Patent No.: US 10,413,192 B2
(45) Date of Patent: Sep. 17, 2019

(54) OBJECT INFORMATION ACQUIRING APPARATUS AND CONTROL METHOD THEREOF

(71) Applicant: CANON KABUSHIKI KAISHA, Tokyo (JP)

(72) Inventor: Koichiro Wanda, Yokohama (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 233 days.

(21) Appl. No.: 14/405,274

(22) PCT Filed: Jun. 26, 2013

(86) PCT No.: PCT/JP2013/068190
§ 371 (c)(1),
(2) Date: Dec. 3, 2014

(87) PCT Pub. No.: WO2014/013867
PCT Pub. Date: Jan. 23, 2014

(65) Prior Publication Data
US 2015/0148652 A1    May 28, 2015

(30) Foreign Application Priority Data
Jul. 17, 2012    (JP) ................. 2012-158988

(51) Int. Cl.
*A61B 5/00* (2006.01)
*A61B 5/145* (2006.01)
(Continued)

(52) U.S. Cl.
CPC ........ *A61B 5/0095* (2013.01); *A61B 5/14542* (2013.01); *A61B 5/743* (2013.01);
(Continued)

(58) Field of Classification Search
CPC . A61B 5/0095; A61B 5/14542; A61B 5/1464; A61B 5/02411
See application file for complete search history.

(56) References Cited

U.S. PATENT DOCUMENTS 5,840,023 A      11/1998  Oraevsky et al. ............ 600/407
6,306,091 B1 *   10/2001  Sumanaweera ..... G01S 7/52023
                                                  128/916
(Continued)

FOREIGN PATENT DOCUMENTS

JP    2002-191599 A    7/2002
JP    2006-023820      1/2006
(Continued)

OTHER PUBLICATIONS

M. Xu et al., "Universal Back-Projection Algorithm for Photoacoustic Computed Tomography", *Physical Review E*, vol. 71, 016706 (Jan. 19, 2005).

(Continued)

*Primary Examiner* — Joseph M Santos Rodriguez
(74) *Attorney, Agent, or Firm* — Venable LLP

(57) ABSTRACT

Provided is an object information acquiring apparatus, including: a light source; a detecting unit that detects an acoustic wave generated from an object which has received an irradiation light from the light source; a processing unit that generates characteristic information on the inside of the object by using the acoustic wave; and a memory unit that records the characteristic information in association with information on the irradiation light.

23 Claims, 12 Drawing Sheets

(51) Int. Cl.
*A61B 8/08* (2006.01)
*A61B 8/00* (2006.01)
*G06F 19/00* (2018.01)

(52) U.S. Cl.
CPC .............. *A61B 8/085* (2013.01); *A61B 8/0825* (2013.01); *A61B 8/403* (2013.01); *A61B 8/42* (2013.01); *A61B 8/4416* (2013.01); *A61B 8/466* (2013.01); *A61B 8/5292* (2013.01); *G06F 19/321* (2013.01)

(56) References Cited

U.S. PATENT DOCUMENTS

| | | | |
|---|---|---|---|
| 6,991,606 B2 | 1/2006 | Kamiyama | |
| 7,515,948 B1 * | 4/2009 | Balberg | A61B 5/0095 600/323 |
| 2004/0010194 A1 | 1/2004 | Kamiyama | |
| 2010/0087733 A1 | 4/2010 | Nakajima | 600/437 |
| 2010/0094561 A1 | 4/2010 | Masumura | 702/19 |
| 2013/0006088 A1 | 1/2013 | Miyasato | |
| 2013/0267856 A1 | 10/2013 | Watanabe et al. | 600/476 |
| 2013/0274585 A1 | 10/2013 | Wanda | 600/407 |
| 2014/0107462 A1 | 4/2014 | Wanda | 600/407 |
| 2014/0196544 A1 | 7/2014 | Wanda | 73/655 |

FOREIGN PATENT DOCUMENTS

| | | |
|---|---|---|
| JP | 2011-206192 A | 10/2011 |
| JP | 2012-061202 | 3/2012 |
| JP | 2012-125447 | 7/2012 |
| WO | 2010/125715 A1 | 11/2010 |

OTHER PUBLICATIONS

Office Action dated Jul. 24, 2018, in counterpart application JP 2017-207179 (7 pages).

Office Action dated Apr. 25, 2017 in counterpart Japanese patent application 2012-061202A, with machine translation.

Office Action dated Jun. 25, 2019, in counterpart application JP 2018-177485 (6 pages).

* cited by examiner

OBJECT INFORMATION ACQUIRING APPARATUS AND CONTROL METHOD THEREOF

TECHNICAL FIELD

The present invention relates to an object information acquiring apparatus and a control method thereof.

BACKGROUND ART

Research on optical imaging techniques is ongoing in medical fields to acquire information on the inside of an object by irradiating light onto the object, and PAT (Photoacoustic Tomography) is one of these techniques. PAT utilizes the photoacoustic effect when a light absorber (a region having a high absorption coefficient) in the object absorbs energy of the irradiated light, expands its volume, generates a photoacoustic wave, and visualizes information related to the optical characteristic values inside the object. To visualize information, an acoustic wave is detected at a plurality of locations surrounding the object, and acquired signals are mathematically analyzed.

If a photoacoustic diagnostic apparatus based on the PAT technique is used, such information as initial sound pressure distribution and light energy absorption density distribution inside the object can be acquired, and the acquired information can be used for specifying a location of a malignant tumor that involves the growth of new blood vessels, for example. In the following, the description on initial sound pressure distribution includes description on light energy absorption density. Generating and displaying a three-dimensional reconstructed image based on such initial sound pressure distribution is useful in knowing the internal state of biological tissue for diagnosis.

On the other hand, along with the recent advancements of information processors and the increase in data capacity, three-dimensional images of the human body, such as CT and MRI, are used at higher frequencies in the medical field. For medical image diagnosis, it is desirable to save all the data for a long period of time in order to compare the test results of a plurality of modalities, and observe progress after surgery. However three-dimensional image data normally has large capacity, and redundant data must be minimized for long term data storage.

For the format of three-dimensional image data, a standard format, such as volume data format, is better than an application-specific format in terms of versatility which allows the use of various software, and easy data analysis. Therefore in a photoacoustic diagnostic apparatus as well, it is preferable to output a three-dimensional image in volume data format.

Now the characteristics of a reconstructed image by PAT will be described. In the case of PAT, if the time variation of an acoustic wave is measured at various points on a closed spatial surface (a spherical measurement surface in particular) that surrounds the entire object, using an ideal acoustic detector (wideband, point detection), the initial sound pressure distribution generated by photo-irradiation can theoretically be completely visualized. It is also known that the initial sound pressure distribution generated by photo-irradiation can be reproduced almost perfectly if columnar or planar measurement is performed on the object, even if a closed space is not used (see NPL 1).

Expression (1) is a partial differential equation called a "photoacoustic wave equation", and by solving this equation, acoustic wave propagation from the initial sound pressure distribution can be described, and where and how the acoustic wave could be detected can be theoretically performed.

[Math. 1]

$$\left(\nabla^2 - \frac{1}{c^2}\frac{\partial^2}{\partial t^2}\right)p(r, t) = -p_0(r)\frac{\partial \delta(t)}{\partial t} \quad (1)$$

where r denotes a position, t denotes time, p(r, t) denotes time variation of the sound pressure, $p_0(r)$ denotes initial sound pressure distribution, and c denotes sound velocity. $\delta(t)$ denotes a delta function that represents the shape of the light pulse.

Reconstructing an image by PAT means deriving the initial sound pressure distribution $p_0(r)$ from the sound pressure pd ($r_d$,t) acquired at a detection point, which in mathematics is called an "inverse problem". The UBP (Universal Back Projection) method, which is a representative image reconstruction method based on PAT, will now be described. The inverse problem to determine $p_0(r)$ can be accurately solved by analyzing the photoacoustic wave equation of Expression (1) in the frequency space. UBP is this result expressed in the time space. Finally Expression (2) shown below is derived.

[Math. 2]

$$p_0(r) = -\frac{2}{\Omega_0}\nabla \cdot \int_{S_0} \hat{n}_0^S dS_0 \left[\frac{p_0(r_0, t)}{t}\right]_{t=|r-r_0|} \quad (2)$$

where $\Omega_0$ denotes a solid angle of the entire measurement area $S_0$ at an arbitrary voxel (unit region).

This expression can be simplified and transformed into Expression (3) shown below.

[Math. 3]

$$p_0(r) = \int_{\Omega_0} b(r_0, t = |r - r_0|) \frac{d\Omega_0}{\Omega_0} \quad (3)$$

where $b(r_0,t)$ denotes projection data, and $d\Omega_0$ denotes a solid angle of a detector $dS_0$ to an arbitrary observation point P. The initial sound pressure distribution $p_0(r)$ can be acquired by performing back projection of this projection data according to the integration of Expression (3).

$b(r_0,t)$ and $d\Omega_0$ are given by Expression (4) and Expression (5) shown below.

[Math. 4]

$$b(r_0, t) = 2p(r_0, t) - 2t\frac{\partial p(r_0, t)}{\partial t} \quad (4)$$

$$d\Omega_0 = \frac{dS_0}{|r-r_0|}\cos\theta \quad (5)$$

where θ is an angle formed by the detector and an arbitrary observation point P.

If the distance between the sound source and the measurement position is sufficiently long with respect to the level of the sound source (long distance sound field approximation), Expression (6) shown below is used.

[Math. 5]
$$p(r_0, t) \ll t \frac{\partial p(r_0, t)}{\partial t} \quad (6)$$

In this case, $b(r_0,t)$ is given by Expression (7) shown below.

[Math. 6]
$$b(r_0, t) = -2t \frac{\partial p(r_0, t)}{\partial t} \quad (7)$$

Thus in the image reconstruction based on PAT, the projection data $b(r_0,t)$ is determined by time-differentiating the detection signal $p(r_0,t)$ acquired by the detector, and is back-projected according to Expression (3), whereby the initial sound pressure distribution $p_0(r)$ is determined (see NPL 1).

Expression (1), used for determining Expression (3), however, assumes "constant sound velocity", "measurement from every direction", "impulse type photo-excitation", "acoustic wave detection in broadband", "acoustic wave detection at a point" and "continuous acoustic wave sampling". In reality it is not easy to implement an apparatus that satisfies these assumptions.

For example, it is actually difficult to acquire acoustic wave detection information on the total closed spatial surface surrounding the entire object. Furthermore, in order to increase the acoustic wave measurement region, the size and number of elements of the acoustic detector, and a signal processing unit and control unit of each element must be increased, which increases manufacturing cost. For these reasons many practical measurement apparatuses based on the PAT technique detect an acoustic wave from an object in a specific direction using a limited sized probe.

An example of such an apparatus is the PAT of a plate type measurement system disclosed in PTL 1. According to PTL 1, light is irradiated onto an object sandwiched by plates, and an acoustic wave is detected by an acoustic wave detector installed on the plate. In some cases the light is irradiated and the acoustic wave is detected for a plurality of times, and measured values are averaged, whereby such an effect as an improvement in the S/N ratio is implemented.

Image qualities (S/N ratio, artifact) of a reconstructed image in a photoacoustic diagnostic apparatus are influenced not only by the above mentioned acoustic wave detection conditions, but also by light irradiation conditions. If light is irradiated from outside an object, the level of light decays from the surface area to a deep part of the object due to the absorption of light by biological tissue. In effect it is difficult to irradiate light onto an object under ideal conditions.

It is possible to estimate the intensity of the irradiated light inside the object. In other words, the extent of decay of the level of irradiated light is determined considering an absorption coefficient according to a segment of the object, and light energy distribution is estimated. However it is difficult to completely eliminate the artifacts and errors of signal values even if the signal values of the photoacoustic wave are corrected based on the estimation result.

Furthermore, data becomes enormous if all factors that could influence the optical system in the imaging apparatus are recorded for the object. In the case of a method of recording and simulating the specifications and settings of each apparatus, the recording method and utilization method could be overly specific. It also involves complicated handling and time to calculate information on the irradiated light from the recorded data.

In the case of using a reconstructed image of the photoacoustic diagnostic apparatus for the purpose of medical diagnosis, it is necessary to know the degree of reliability and the influence of optical conditions within a reconstructed image. However conventionally photo-irradiation conditions depend on the design and specifications of the apparatus, and are recorded as apparatus-dependent information (e.g. setting values and imaging conditions of the apparatus). It is also time consuming to analyze information when conditions of the irradiated light are reproduced based on the recorded information. In photoacoustic diagnostic apparatuses as well, no technique is available to store information on individual irradiated light for each reconstructed image.

According to the technique disclosed in PTL 2, virtual light source information is stored to render computer graphics for creating a three-dimensional image. However information on irradiated light for imaging inside biological tissue cannot be stored as information corresponding to the reconstructed image. Therefore the only way to display and analyze a reconstructed image considering the conditions of irradiated light is to record redundant data which depends on the apparatus, and to perform time consuming analysis processing.

CITATION LIST

Patent Literature

PTL 1: U.S. Pat. No. 5,840,023
PTL 2: Japanese Patent Application Laid-Open No. 2006-023820

Non Patent Literature

NPL 1: Physical Review E 71, 016706 (2005)

SUMMARY OF INVENTION

Technical Problem

In the case of imaging by the photoacoustic diagnostic apparatus, scattering and decaying of transmitted light occur inside the object, and a tendency of the scattering and decaying depends on the region of the object, and is not uniform (particularly in a shallow region near the irradiation surface). Therefore conditions of generating a photoacoustic wave differ depending on the region, even within the volume data acquired by reconstruction. It is also difficult to completely clear artifacts generated under various conditions related to photo-irradiation and acoustic wave acquisition, and to completely clear errors of calculated values from the three-dimensional reconstructed image in which the initial sound pressure distribution in the object is generated.

In order to reconstruct a good image under these conditions, it is necessary to estimate the quantity of light at each location in the object, and store the information on the irradiated light along with the reconstructed image as data for estimating the quantity of light. However the use of redundant data and an enormous amount of efforts are required to display and analyze the reconstructed image, since no technique is available to record information on the irradiated light during imaging in a standard and versatile format without using a format that depends on the measurement apparatus.

With the foregoing in view, it is an object of the present invention to record information on the irradiated light used in photoacoustic tomography in correspondence with the reconstructed image, so that the information can be easily used for displaying and analyzing the reconstructed image.

Solution to Problem

The present invention provides an object information acquiring apparatus, comprising:
a light source;
a detecting unit configured to detect an acoustic wave generated from an object which has received an irradiation light from the light source;
a processing unit configured to generate characteristic information on the inside of the object by using the acoustic wave; and
a memory unit configured to record the characteristic information in association with information on the irradiation light.

The present invention also provides a method for controlling an object information acquiring apparatus, comprising:
a step of emitting an irradiation light from a light source to an object;
a step of detecting an acoustic wave generated from the object which has received the irradiation light;
a step of generating characteristic information on the inside of the object by using the acoustic wave; and
a step of storing the characteristic information in association with the information on the irradiation light.

Advantageous Effects of Invention

According to the present invention, information on the irradiated light used in photoacoustic tomography can be recorded in correspondence with the reconstructed image, so that the information can be easily used for displaying and analyzing the reconstructed image.

Further features of the present invention will become apparent from the following description of exemplary embodiments with reference to the attached drawings.

DESCRIPTION OF EMBODIMENTS

Preferred embodiments of the present invention will now be described with reference to the drawings. Dimensions, materials, shapes and relative positional relationships of the components described below could be appropriately modified according to the configuration and various conditions of the apparatus to which the present invention is applied, and are not intended to limit the scope of the invention.

An object information acquiring apparatus of the present invention includes an apparatus that receives an acoustic wave (typically an ultrasonic wave) generated inside an object by irradiating light (electromagnetic wave) onto the object, and acquires the object information distribution as image data.

In the case of an apparatus using the photoacoustic effect, object information is a generation source distribution of an acoustic wave generated by the photo-irradiation, an initial sound pressure distribution in the object, a light energy absorption density distribution derived from the initial sound pressure distribution, an absorption coefficient distribution, and a concentration information distribution of a substance constituting a tissue. The density information distribution of a substance is, for example, an oxygen saturation distribution or an oxygenated/deoxygenated hemoglobin concentration distribution. This characteristic information is called "object information".

The acoustic wave according to the present invention is a compressional wave, and includes an elastic wave called a "sound wave", an "ultrasonic wave" and an "acoustic wave". An example is an acoustic wave that is generated inside an object when a near-infrared ray is irradiated inside the object. An acoustic wave generated by the photoacoustic effect is called a "photoacoustic wave" or a "photoacoustic ultrasonic wave". An acoustic detector (e.g. probe) receives an acoustic wave generated in the object.

Embodiments

A photoacoustic diagnostic apparatus according to an embodiment detects an acoustic wave which is generated by irradiating light onto an object, and generates a three-dimensional reconstructed image. In this embodiment, by one imaging process, information on the irradiated light that can be used for a coordinate system, which is relatively determined for an imaging region, is generated along with the detected acoustic wave signal. Furthermore, the information on the coordinate system and the irradiated light is stored as recording data, so that information based on volume data of the reconstructed image can be easily displayed and analyzed.

(Functional Block Diagram)

Figure 1:
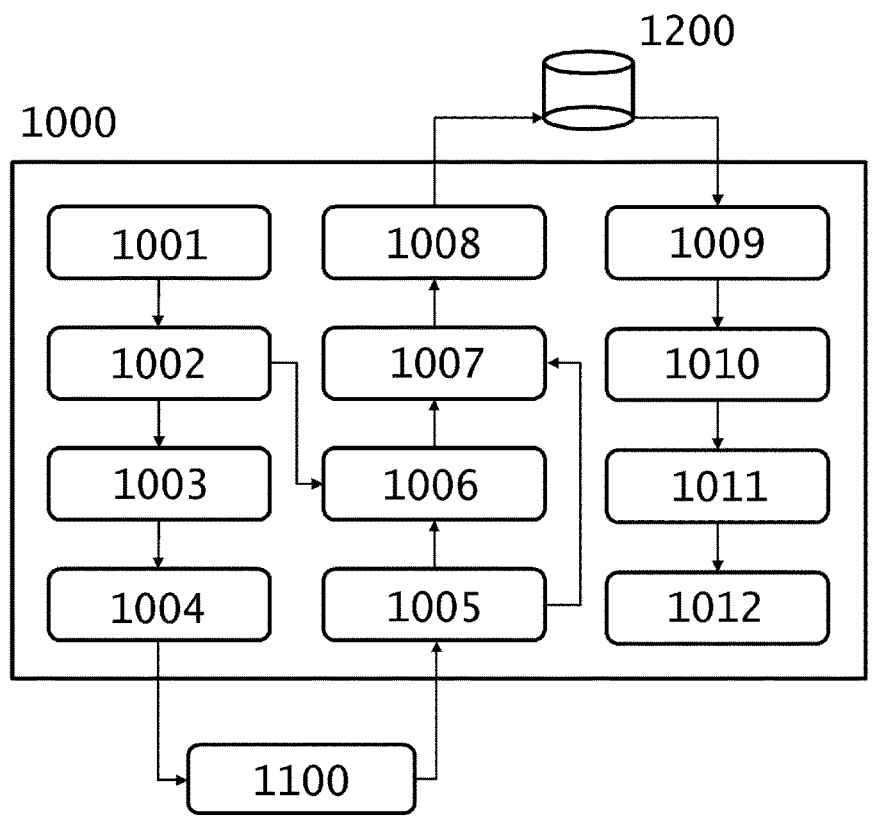
FIG. 1 is a diagram depicting functional blocks of a photoacoustic diagnostic apparatus.
Figure 2:
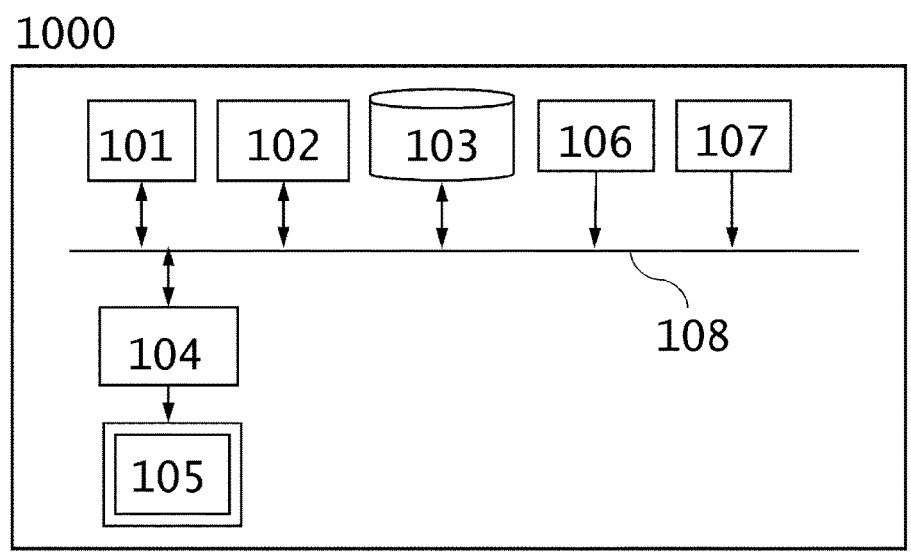
FIG. 2 is a diagram depicting a configuration example of an information processing unit.
Figure 3:
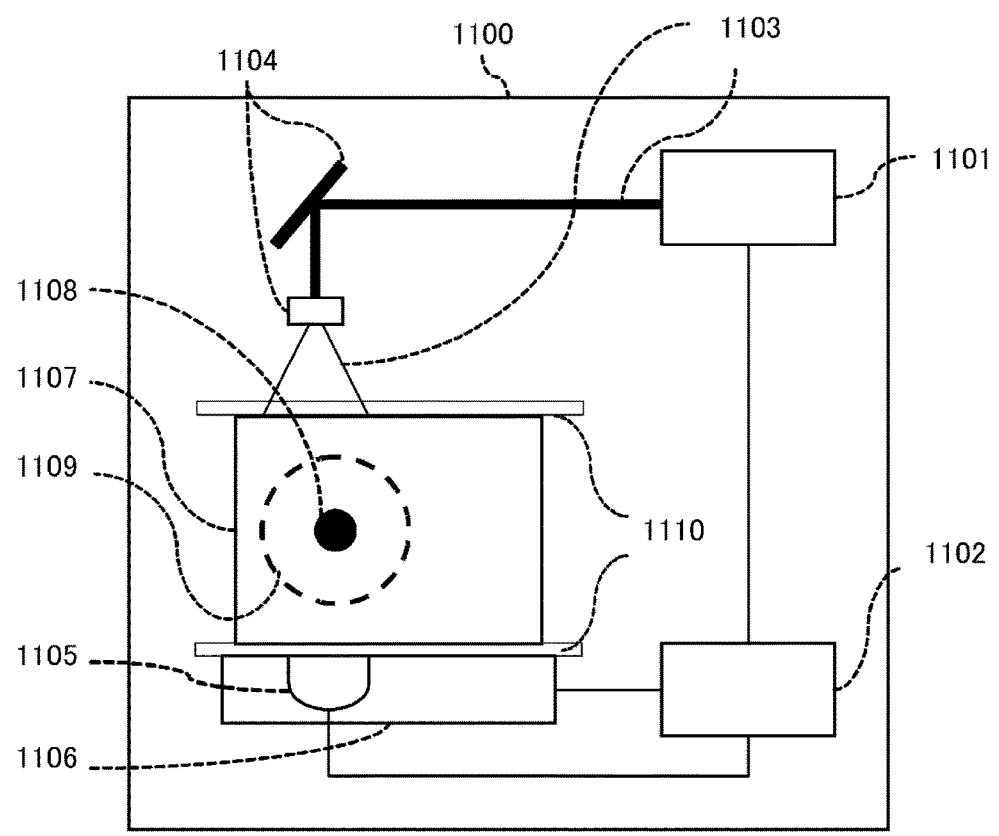
FIG. 3 is a diagram depicting a configuration example of a photoacoustic wave signal measuring unit.

FIG. 1 shows the functional blocks of the photoacoustic diagnostic apparatus. The photoacoustic diagnostic apparatus is comprised of an information processing unit 1000 and an acoustic wave signal measuring unit 1100. FIG. 2 and FIG. 3 show an example of the apparatus configuration to implement each functional block. FIG. 2 is an example of the apparatus configuration to implement the information processing unit 1000. FIG. 3 is an example of the apparatus configuration to implement the photoacoustic wave signal measuring unit 1100.

The photoacoustic wave signal measuring unit 1100 measures an acoustic wave signal. The photoacoustic wave signal measuring unit 1100 controls acoustic wave measurement based on the acoustic wave measurement method instructed from the information processing unit 1000, generates photoacoustic wave signal information based on an acoustic wave detected by each element of an acoustic wave detector 1105, and transmits the photoacoustic wave signal information to the information processing unit 1000.

Here the acoustic wave detector 1105 is a probe to detect an acoustic wave, for example. The photoacoustic wave signal information corresponds to information of the receiving element, such as an acoustic wave signal detected by an element of the probe, information on the position of the element disposed on the receiving surface of the acoustic wave detector 1105, and information on sensitivity and directivity. Conditions for acquiring an acoustic wave signal, such as imaging parameters to acquire the acoustic wave, are also included in the acoustic wave signal information.

If an acoustic wave is detected by the photoacoustic wave signal measuring unit 1100 by moving the probe, the scanning region where the probe detected the acoustic wave is handled as a reception region, and the position of an element which detected the acoustic wave is handled as an element position in the reception region. In this case, the photoacoustic wave signal information includes a position of the reception region in a coordinate system inside the apparatus, and an element position in the reception region. The photoacoustic wave signal information also includes information on control of the light source, and information on compression of the object, as the conditions for acquiring an acoustic wave signal.

For the acoustic wave signal included in the photoacoustic wave signal information, the received acoustic wave signal may be transmitted directly, or may be transmitted after correcting the sensitivity of the element or the gain. If irradiation of light and detection of the acoustic wave signal are repeated a plurality of times for a same position in one imaging process, the average value of the detected acoustic signal values may be transmitted. Even if the probe is moved, a value of the acoustic wave signal detected by an element having a same capability as the previous element at the same position in the reception region may be included in the values to determine the average value.

Of the photoacoustic wave signal information, information that can be regarded as a statistical constant in the embodiment may be stored in a main memory 102 or magnetic disk 103 of the information processing unit 1000 in advance, and be read and used when the image is reconstructed. Information that is dynamically determined each time an image is photographed, on the other hand, is transmitted from the photoacoustic wave signal measuring unit 1100 to the information processing unit 1000 every time. For example, a position of an element on a receiving surface of the acoustic wave detector 1105 can be stored in the information processing unit 1000 in advance.

The information processing unit 1000 acquires an instruction on the imaging from the user, determines an acoustic wave measurement method considering the image quality of the reconstructed image, and instructs imaging to the photoacoustic wave signal measuring unit 1100. The information processing unit 1000 also performs three-dimensional image reconstruction processing using the photoacoustic wave signal information received from the photoacoustic wave signal measuring unit 1100, and displays the image.

The functional blocks of the information processing unit 1000 will now be described. The information processing unit 1000 includes an imaging instruction information acquiring unit 1001, a reconstruction method determining unit 1002, a photoacoustic wave measurement method determining unit 1003, a photoacoustic wave measurement method instructing unit 1004, a photoacoustic wave signal information acquiring unit 1005, and a reconstruction processing unit 1006. The information processing unit 1000 further includes a data generating unit 1007, a data recording unit 1008, a data acquiring unit 1009, a data analyzing unit 1010, a display information generating unit 1011, and a display unit 1012.

The imaging instruction information acquiring unit 1001 acquires an instruction on imaging that the user inputs via an input unit 106. The instruction on imaging is, for example, information to specify an imaging region in the acoustic wave signal measuring unit 1100, or information to specify an image quality of the reconstructed image.

A method for specifying an imaging region is, for example, the user specifying only a two-dimensional region on a compressing plate of an object, and determining a rectangular parallelepiped imaging region based on the thickness of the object measured by the photoacoustic wave signal measuring unit 1100. Another possible method is information processing unit 100 storing a region, specified in the coordinate system in the photoacoustic wave signal measuring unit 1100, as preset information, and specifying an identifier of the region.

An example of information to specify the image quality of the reconstructed image is the number of acoustic wave signals used for the reconstruction processing. The number of acoustic wave signals used for each point in the reconstruction region, or a relative detection position for each point of the acoustic wave signal, which is required for each point, may be specified. The detection position of the acoustic wave signal may be specified as an effective acoustic wave signal. A condition may be set under which acoustic wave detection signals assemble at all the element positions on the reception region, which can be included in the range of directivity of the element of the probe.

These conditions on the acoustic wave signal can limit the degree of an artifact and bias. Furthermore, depending on the reconstruction algorithm, parameters may be set according to the characteristics of the reconstruction algorithm or the acoustic characteristics of an environment in which the acoustic wave is detected, or the reception conditions may be added. For the user to input the conditions, the user may select an image quality level where these conditions are preset in advance.

The imaging instruction information acquiring unit 1001 acquires imaging instruction information from the user, and transmits the information to the reconstruction method determining unit 1002.

Using the imaging instruction information and information on image quality, the reconstruction method determining unit 1002 determines an appropriate reconstruction method based on the capability of the photoacoustic wave signal measuring unit 1100, and the capability of the reconstruction processing unit 1006 which are stored in advance. The reconstruction method determining unit 1002 generates reconstruction instruction information based on the determined reconstruction method, and transmits the information to the reconstruction processing unit 1006. The reconstruction method determining unit 1002 transmits the reconstruction instruction information and the imaging instruction information to the photoacoustic wave measurement method determining unit 1003. The imaging instruction information may be directly transmitted from the imaging instruction information acquiring unit 1001 to the photoacoustic wave measurement method determining unit 1003.

Examples of the reconstruction instruction information are information on a reconstruction region which corresponds to an imaging region, and information on parameters of reconstruction processing, such as a reconstruction algorithm, and the number and pitch of voxels (unit region, pixels in the case of two-dimensional data) to be reconstructed. If the acoustic wave measurement environment and reconstruction processing in an imaging region cannot be handled in a same processing, the imaging region may be segmented into a plurality of reconstruction regions, and a separate reconstruction instruction information may be generated for each region.

The photoacoustic wave measurement method determining unit 1003 determines an acoustic measurement method of the photoacoustic wave signal measuring unit 1100 based on the acquired reconstruction instruction information and the imaging instruction information. For example, setting information related to irradiation light control, such as parameters on the light source and the optical path, is determined.

When signals are acquired in a wide range by scanning with a probe, the photoacoustic wave measurement method determining unit 1003 calculates a scanning region, which is required for reconstructing the image using the instructed reconstruction method for the instructed imaging region, from the imaging instruction information and the reconstruction instruction information. In this case, the scanning region is normally one surface of the rectangular parallelepiped to be photographed, but this is not always the case.

The photoacoustic wave measurement method determining unit 1003 also determines a pitch of an element position in the reception region. Further, the photoacoustic wave measurement method determining unit 1003 may determine parameters for the acoustic wave acquiring conditions related to the image quality of the reconstruction processing, and a method for correcting a signal.

The photoacoustic wave measurement method determining unit 1003 generates acoustic wave measurement information integrating the instruction information required for measuring these acoustic wave signals, and transmits the acoustic wave measurement information to the photoacoustic wave measurement method instructing unit 1004. In this embodiment, the acoustic wave measurement information is generated for each photography process, but acoustic wave measurement information created in advance may be selected, and the identifier thereof may be transmitted.

The photoacoustic wave measurement method instructing unit 1004 transmits the acoustic wave measurement instruction information to the photoacoustic wave signal measuring unit 1100 to instruct the acoustic wave measurement. The acoustic wave measurement instruction information itself may be transmitted or an identifier thereof may be transmitted.

The photoacoustic wave signal information acquiring unit 1005 receives the photoacoustic wave signal information from the photoacoustic wave signal measuring unit 1100, and transmits the photoacoustic wave signal information to the reconstruction processing unit 1006. The photoacoustic wave signal information acquiring unit 1005 also transmits information on the irradiation light to the imaging region to the data generating unit 1007.

The reconstruction processing unit 1006 generates a three-dimensional reconstructed image (volume data) for each point in the image reconstruction region, using only the selected acoustic wave signals. In other words, the reconstruction processing unit 1006 performs reconstruction processing using the photoacoustic wave signal information according to the reconstruction instruction information. The image reconstruction processing may be a time domain method or a Fourier domain method only if a three-dimensional image is reconstructed based on the analysis solution. Thereby a three-dimensional image that indicates optical characteristic value distribution (initial sound pressure distribution and absorption coefficient distribution derived therefrom) inside the object can be generated, and the difference of composition inside the object can be displayed. Light intensity may be corrected at this time.

If the setting of the reconstruction region and reconstruction parameters need be changed or corrected because the photoacoustic wave signal measuring unit 1100 failed in the acoustic wave measurement, for example, the change or correction can be executed at this time. If information on the acoustic wave measurement executing state is included in the photoacoustic wave signal information, the necessity of correction can be determined by comparing this information with the reconstruction instruction information.

The reconstruction processing unit 1006 transmits the generated reconstructed image to the data generating unit 1007.

The data generating unit 1007 generates recording data based on the reconstructed image received from the reconstruction processing unit 1006, and the information on photo-irradiation onto the imaging region acquired from the photoacoustic wave signal information acquiring unit 1005.

The recording data is generated by attaching information on the photo-irradiation to volume data for each voxel (unit region). The data format that can be used is DICOM (Digital Imaging and Communications in Medicine), which is a standard for medical imaging. Information on the photoacoustic diagnostic apparatus is not included in the standard specification, but data can be handled easily without redundancy, while maintaining versatility of volume data if information on photo-irradiation is stored in private tags. Thereby such general functions as image display and analysis according to the capability of the viewer corresponding to the DICOM image can be used. If a viewer corresponding to information on photo-irradiation is used, the display and analysis of information on the photo-irradiation can be performed using a same data file.

The data generation unit 1007 transmits the generated recording data to the data recording unit 1008.

The data recording unit 1008 stores the recording data in such a storage medium as a magnetic disk 103 as a recording data file 1200. The storage medium can be any type, and the recording data may be recorded by an external unit via a network.

The data acquiring unit 1009 acquires recording data from the recording data file 1200 to the information processing unit 1000, and transmits the recording data to the data analyzing unit 1010.

The data analyzing unit 1010 extracts a reconstructed image or information on photo-irradiation from the received recording data based on the data format, and transmits the extracted information to the display information generating unit 1011.

The display information generating unit 1011 generates the reconstructed image and the display information based on the information on photo-irradiation.

Image processing is performed on a reconstructed image if necessary. For example, if the reconstructed image is a three-dimensional image, such as volume data, then volume rendering, multi-planar reconstruction or maximum intensity projection, for example, is used. Image processing is performed considering a brightness value that can be displayed on the display screen. The reconstructed image based on the photo-irradiation may be displayed integrating with other information.

Examples of the display information based on the information on the irradiation light are information on the direction of the light which makes it easier to identify the irradiation position of the light and the irradiating surface, and information on the light intensity. A line to represent the optical axis corresponding to the irradiation angle of the light may be generated and added to the display information. Various display information can be generated so that information is displayed based on the information on the irradiated light, or analysis result information is displayed.

The display information generating unit 1011 transmits the display information to the display unit 1012.

The display unit 1012 is a display device for displaying the generated display information, such as a graphic card, a liquid crystal display or a CRT display, and displays the display information transmitted from the display information generation unit 1011.

The photoacoustic wave signal measuring unit 1100 and the information processing unit 1000 may be integrated. A function to perform measurement by a modality other than photoacoustic tomography (e.g. ultrasonic diagnosis) may be added to the apparatus configuration according to this embodiment.

FIG. 2 is a diagram depicting a basic configuration of a computer for implementing the function of each component of the information processing unit 1000 by software.

A CPU 101 controls each composing element of the information processing unit 1000. The main memory 102 stores a control program which the CPU 101 executes, or provides a work area for the CPU 101 to execute programs. A magnetic disk 103 stores an operating system (OS), a device driver for peripheral apparatuses, and programs to perform the processing in the flow chart, which is described later. A display memory 104 temporarily stores display data for a monitor 105.

The monitor 105 is a CRT display or a liquid crystal monitor, for example, and displays an image based on data from the display memory 1204. An input unit 106 accepts pointing input from a mouse, or input of characters from a keyboard by the operator.

An I/F 107 is for exchanging various data between the information processing unit 1000 and external units, and is constituted by IEEE 1394, USB and Ethernet® ports, for example. The data acquired via the I/F 107 is loaded to the main memory 102. The above composing elements are communicably interconnected by a common bus 108.

FIG. 3 is a diagram depicting an example of the configuration of the photoacoustic wave signal measuring unit 1100. This configuration implements the photoacoustic wave diagnostic apparatus.

The light source 1101 is a light source of the irradiation light to an object, such as a laser or a light emitting diode. For the irradiation light, an irradiation light having a wavelength, at which the degree of absorption of the light by a specific component out of the components constituting the object is expected to be high, is used.

The control unit 1102 controls the light source 1101, the optical apparatus 1104, the acoustic wave detector 1105 and the position controlling unit 1106. The control unit 1102 also amplifies an electric signal of the photoacoustic wave acquired by the acoustic wave detector 1105, and converts the analog signal into a digital signal. The control unit 1102 also performs various types of signal processing and various types of correction processing. The control unit 1102 also transmits the acoustic wave signal from the photoacoustic wave signal measuring unit 1100 to such an external apparatus as the information processing unit 1000 via an interface, which is not illustrated.

The control factors for the light source are, for example, the timing, waveform and intensity of laser irradiation. The control unit 1102 also performs control to synchronize the signal detection by the acoustic wave detector 1105 with the laser irradiation timing. The acoustic wave signals of each element which are acquired by irradiating the laser a plurality of times may be added and averaged, so as to determine a mean value of the acoustic wave signals of each element.

The optical apparatus 1104 is, for example, a mirror to reflect light, or a lens to collect or expand light or to change the shape of a light beam. The optical apparatus can be arbitrary provided only that the light 1103 emitted from the light source can be irradiated onto the object 1107 in a desired form.

A plurality of light sources 1101 and a plurality of optical apparatuses 1104 may be disposed so that light is irradiated onto the imaging regions in various directions. The irradiated light from the light source 1101 may be propagated using such an optical wave guide as optical fiber. If there is a plurality of light sources, an optical fiber may be provided for each light source, or light from the plurality of light sources may be propagated collectively by one fiber.

If the light 1103 generated by the light source 1101 is irradiated onto the object 1107 via the optical apparatus 1104 under control of the control unit 1102 in this configuration, the light absorber 1108 in the object absorbs the light and emits the photoacoustic wave 1109. In this case, the light absorber 1108 corresponds to the sound source.

The acoustic wave detector 1105 is arbitrary provided only that an acoustic wave can be detected, and examples are a transducer using the piezoelectric phenomena, a transducer using the resonance of light, and a transducer using the change of capacitance. The acoustic wave detector 1105 may directly contact the object 1107 or may detect the photoacoustic wave 1109 via a plate 1110 for compressing the object.

In the acoustic wave detector used in this embodiment, a plurality of elements are two-dimensionally arrayed. By using such two-dimensionally arrayed elements, an acoustic wave can be detected simultaneously at a plurality of locations, detection time can be decreased, and the influence of vibration of the object, for example, can be reduced. An acoustic impedance matching agent, such as gel or water, may be used between the acoustic wave detector 1105 and the object, so as to suppress the reflection of the acoustic wave.

Here the photo-irradiation region on the object and the acoustic wave detector 1105 may be movable. To move the photo-irradiation region, a movable mirror is used as the optical apparatus 1104 or the light source itself is mechanically moved, for example. The position of the acoustic wave detector 1105 can be moved by the position controlling unit 1106. An example of the position controlling unit 1106 is a mechanism to move the acoustic wave detector 1105 on the plate 1110 by a motor based on the information of the position sensor.

The position of the photo-irradiation region and the position of the acoustic wave detector 1105 are synchronously controlled by the control unit 1102. Thereby light can be irradiated over a wide range, and the photoacoustic wave can be detected by the acoustic wave detector which is located in an appropriate position with respect to the irradiation region. The control unit 1102 also generates information on the irradiation light to the imaging region.

To move the probe, any moving method can be used provided only that an acoustic wave signal detected by from an element at each position on the reception region can be regarded as the acoustic wave signal from the element that detected the acoustic wave at the probe which positioned the element in this position. For example, if the element surface of the probe is rectangular, the probe is moved for a size of the vertical width or the horizontal width of the rectangle at a time, and is stopped at each position after the move, and an acoustic wave is detected there, that is using a step and repeat method. By matching the detection signal at each position, the same effect as using a large sized probe can be implemented. The measurement may be performed while continuously moving the probe.

In this embodiment, an acoustic wave required for reconstructing an image in an imaging region specified by the user via the input unit 106 is acquired. The imaging region is a three-dimensional region specified at each imaging process, within a region where the object can be photographed based on the specification of the imaging apparatus.

The method for inputting the imaging region is arbitrary. For example, the coordinates of each vertex of a rectangular parallelepiped to be the imaging region may be inputted, or a mathematical formula to indicate the imaging region, may be inputted. The imaging area may be specified by the user, specifying a rectangular region by mouse on an image of the object which is photographed by a camera via a transparent plate, and measuring the depth of the object (thickness from the plate) in the region. The imaging region need not always be a rectangular parallelepiped.

The processing procedure of this embodiment will now be described with reference to the drawings and the flow charts in FIG. 4 to FIG. 12. According to this embodiment, the imaging processing is executed for a specified imaging region, conditions of the irradiation light used for the reconstructed image are stored, and the stored data is utilized.

Figure 4:
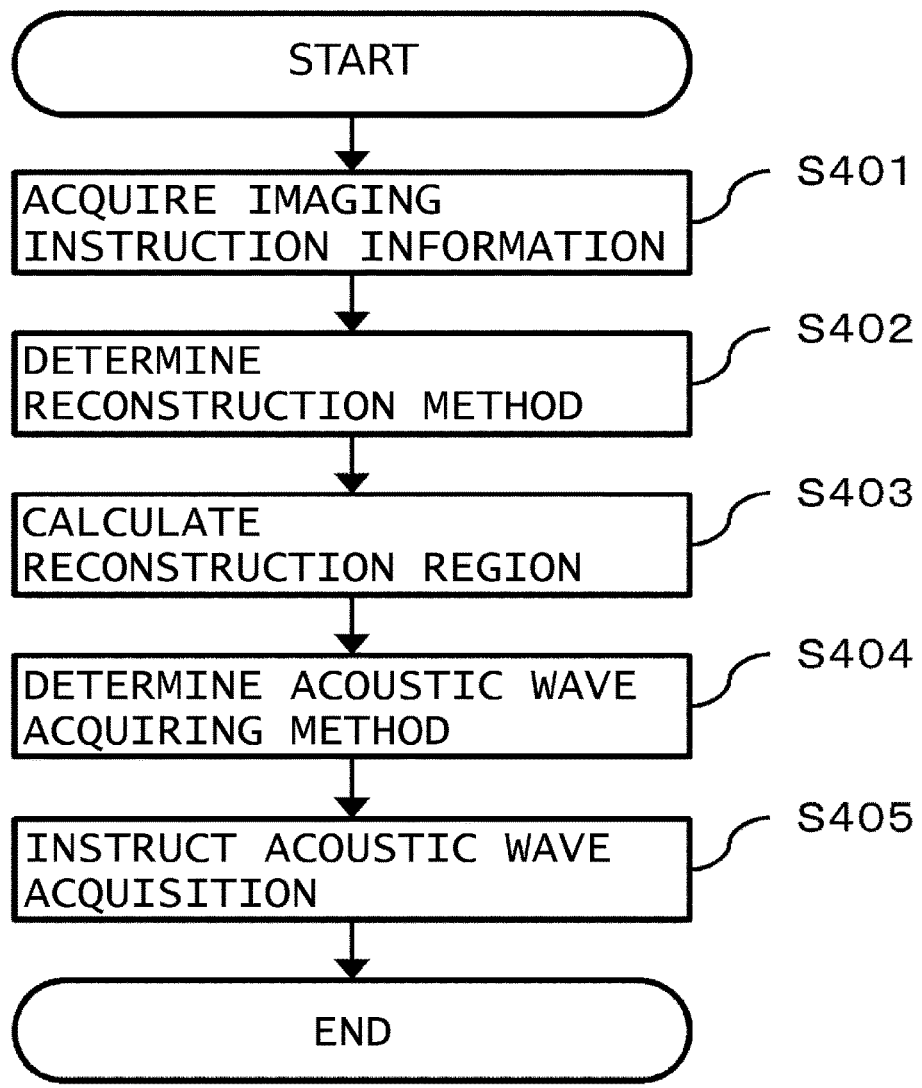
FIG. 4 is a flow chart depicting a processing procedure from starting imaging to instructing acquisition.

FIG. 4 is a flow chart depicting a procedure when the information processing unit 1000 determines the reconstruction method and the photoacoustic wave acquiring method after the user has inputted an operation for imaging, and transmits the determined methods to the photoacoustic wave signal measuring unit 1100.

The flow chart in FIG. 4 starts with the following state. First an operator (technician) secures an object (e.g. breast of an examinee) with a holding plate, then sets parameters on imaging and image quality via the input unit 106, and instructs the start of imaging.

In step S401, the imaging instruction information acquiring unit 1001 acquires setting information on the imaging and setting information on the image quality as the imaging instruction information. Then the imaging instruction information acquiring unit 1001 transmits the acquired imaging instruction information to the reconstruction method determining unit 1002. An example of the imaging instruction information is the imaging parameters on the imaging region and the photoacoustic wave acquisitions. An appropriate photo-irradiation method may be automatically set by the imaging apparatus, instead of being set by the user. The intensity and angle of the laser are set within a range that the apparatus can process. Information on an acoustic wave signal related to the image quality can also be set.

In step S402, the reconstruction method determining unit 1002 determines a reconstruction method based on the imaging instruction information and the pre-stored information on the photoacoustic wave signal measurement by the photoacoustic wave signal measuring unit 1100.

Here the information on the photoacoustic wave signal measurement is information on the photoacoustic wave signal measuring capability. For example, concerning a photographable region, information on the position and size of the photographable region, a region where the probe can be scanned, and a range of the region where the laser can be irradiated are included in this information. Concerning irradiation light, such information as the number of irradiated beams, wave length, intensity (density distribution), angle of irradiation light that can be controlled, signal processing capability of the probe, such as moving velocity and acoustic wave acquisition capability, and laser irradiation interval are included.

The reconstruction method determining unit 1002 determines a reconstruction method that can be executed with the specified image quality when the imaging region included in the imaging instruction information is the reconstruction region. The reconstruction method to be determined includes algorithms and parameters of the reconstruction processing. A correction method (e.g. light distribution correction), which is additionally executed, can also be determined.

In step S403, a reconstruction region for which reconstruction processing is performed during imaging is calculated. Normally the imaging region becomes the reconstruction region. However in some cases, the imaging region and the reconstruction region are different. For example, when both the sufficient imaging region and the image quality must be implemented, or when the capability of the apparatus is insufficient for the required conditions, such as the reconstruction algorithm types and parameters, the imaging region and the reconstruction region are different. In order to decrease the reconstruction processing time and to decrease the time of the entire imaging processing, a region of which image quality is obviously poor may be eliminated from the reconstruction region. The reconstruction method determining unit 1002 generates information for specifying the calculated region as information on the reconstruction region.

In this embodiment, a case when the boundary surface where the lights of the imaging region and the reconstruction region are irradiated matches with the boundary surface of the object will be described. If the inside of the object is specified as the imaging region, however, the irradiation light that reaches the imaging region is determined by calculating the transmitted scattering of light inside the object. In this case, the transmitted scattering in the biological tissue is calculated based on the energy distribution of Gaussian scattering, and the result is regarded as information on the irradiation of light at each position on the boundary of the reconstruction region.

The reconstruction method determining unit 1002 transmits the determined information on the reconstruction method and reconstruction region to the reconstruction processing unit 1006 and the photoacoustic wave measurement method determining unit 1003.

In step S404, the photoacoustic wave measurement method determining unit 1003 determines a method for controlling the photoacoustic wave measuring unit 1100 required for acquiring an acoustic wave in the generated reception region, and generates this method as information on photoacoustic wave acquisition. For example, a method for scanning the probe and a method for controlling irradiation of the light are determined. The photoacoustic wave measurement method determining unit 1003 transmits the information on photoacoustic wave acquisition to the photoacoustic wave measurement method instructing unit 1004.

Now a relationship between the irradiation light and the imaging region, which is determined by the information on photoacoustic wave acquisition determined by the photoacoustic wave measurement method determining unit 1003, based on the imaging region specified by the user, will be described with reference to FIG. 5.

Figure 5:
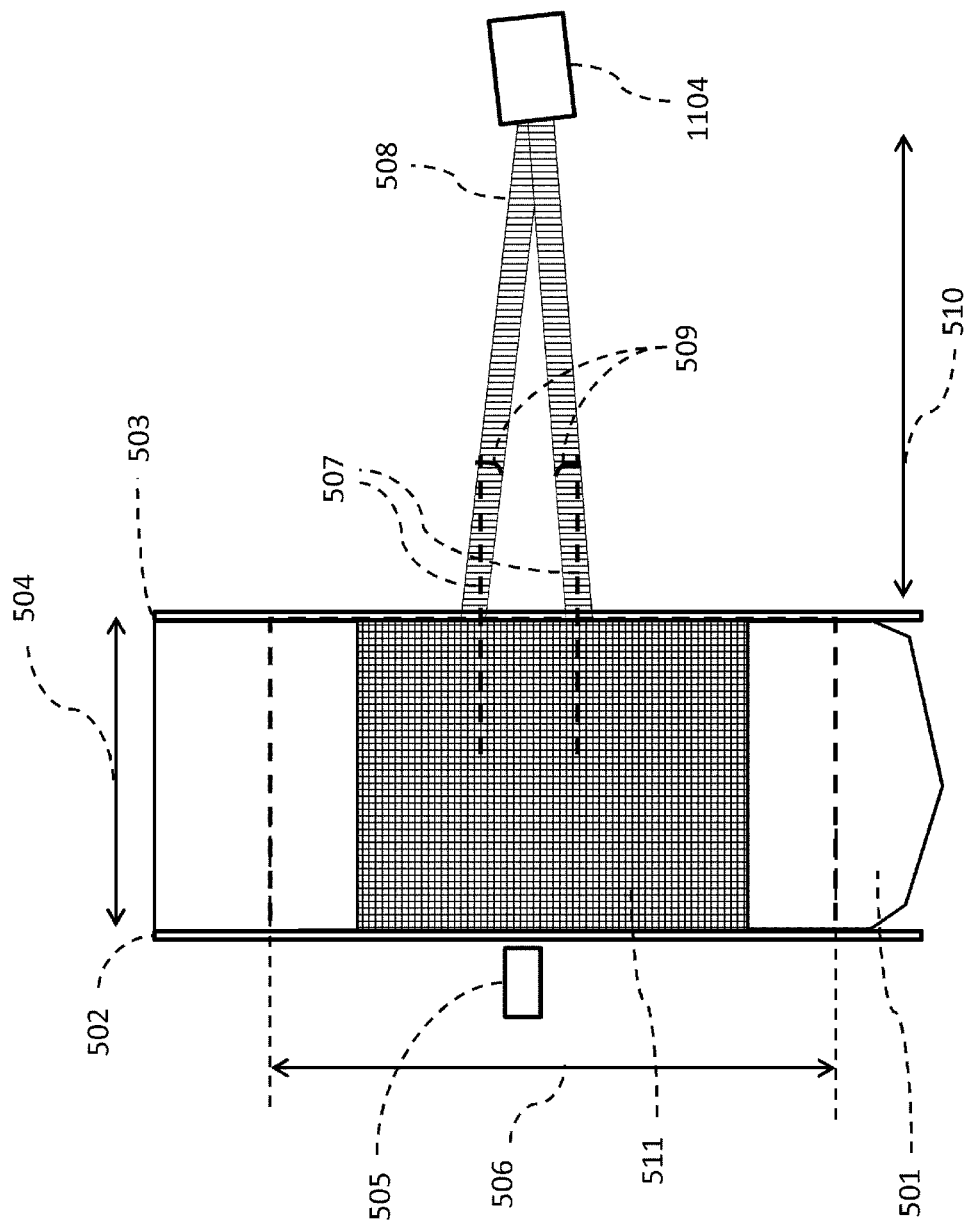
FIG. 5 is a diagram depicting a relationship between an object, an imaging region and an irradiated light.

In FIG. 5, an object 501 which is a part of an examinee is secured to the imaging apparatus. The reference numeral 502 is a holding plate, and is also the scanning surface of the probe. An acoustic wave, refraction of light and decay are generated depending on the thickness of the scanning surface 502. Since all of these do not have influence on essential points of explanation, they are not described in detail here. The holding plate 503 sandwiches the object 501 with the scanning surface 502, and holds the object 501, and the holding plate 503 and the scanning surface 502 correspond to the plates 1110 in FIG. 3. By using the holding plate 503, the boundary of the imaging region and the boundary of the biological tissue can be approximately matched. Furthermore, light intensity can be calculated easily since the boundary becomes a plane.

The reference numeral 504 denotes a space between the scanning surface 502 and the holding plate 503. The depth of the photography region viewed from the scanning surface can be calculated by measuring the space 504. The shape and size of the object, the imaging region, and the three-dimensional position of the imaging region can be specified by an arbitrary method. Any method, such as using a sensor that measures a shape and size, or a method of deriving the shape and size from a camera image by image processing, can be used, as long as the imaging region and the reconstruction region can be specified and associated with the information on the irradiation light in the apparatus.

The probe 505 constitutes the acoustic wave detector 1105, and detects an acoustic wave by moving on the scanning region of the scanning surface. The reference numeral 506 denotes the height of the scanning region of the probe, that is, a height of the scanning region in the vertical direction in FIG. 5. The height 506 is determined from the region on the reception surface, which is a part of the control parameters calculated by the photoacoustic wave measurement method determining unit 1003.

The scanning region need not always match with the size of the boundary surface of the imaging region. This depends on the range of the voxels to be constructed, from which the photoacoustic wave required for the reconstruction processing is acquired. Depending on this setting, the scanning region could be slightly larger or slightly smaller than the imaging region.

The reference numeral 507 denotes a normal line to the boundary surface of the imaging region on the side to which the irradiation light 508 is irradiated. If the imaging region and the reconstruction region match, this normal line is also a normal line to the boundary surface of the reconstruction region. An incident angle 509 of the light with respect to the imaging region corresponds to an incident angle of the irradiated light with respect to the boundary surface of the reconstruction region. The incident angle 509 may be constant depending on the specification of the optical apparatus 1104. However if the relative positional relationship between the imaging region and the optical apparatus 1104 changes as shown in FIG. 5, the incident angle changes depending on the irradiated light.

The reference numeral 510 denotes a distance between the holding plate 503 and an emitting spot of the optical apparatus 1104. The distance 510 changes depending on the compressing state by the holding plate 503, even if the position of the emitting spot to emit the irradiation light of the optical apparatus 1104 and emission angle are determined. As a result, if a diffused light is used as the irradiation light, for example, the size of the irradiation surface on the imaging region may change according to the distance 510. It is preferable that the holding plate 503 has a high light transmittance. The incident angle of the irradiation light is determined considering the refraction of light when the light transmits through the holding plate.

The imaging region 511 is a region which the user specifies in the imaging instruction information. The photoacoustic wave measuring unit 1100 controls the photo-irradiation position and the probe position so that the reconstructed image of the imaging region 511 can be acquired. The number of times of photo-irradiation and photoacoustic wave acquisition, positions, directions and the number of rays which are irradiated at the same time can be determined in various ways according to the reconstruction methods or the like.

Here description with reference to FIG. 4 continues. In step S405, the photoacoustic wave measurement method instructing unit 1004 generates acoustic wave measurement instruction information based on the information on the photoacoustic wave acquisition, and transmits the acoustic wave measurement instruction information to the photoacoustic wave measuring unit 1100. The acoustic wave measurement instruction information is constituted by commands and parameters to instruct the photoacoustic wave measuring unit 1100 to acquire an acoustic wave, for example.

By the above described procedure, processing when the information processing unit 1000 determines the reconstruction method and the photoacoustic wave acquisition method, and transmits the determined methods to the photoacoustic wave measuring unit 1100, can be implemented.

Figure 6:
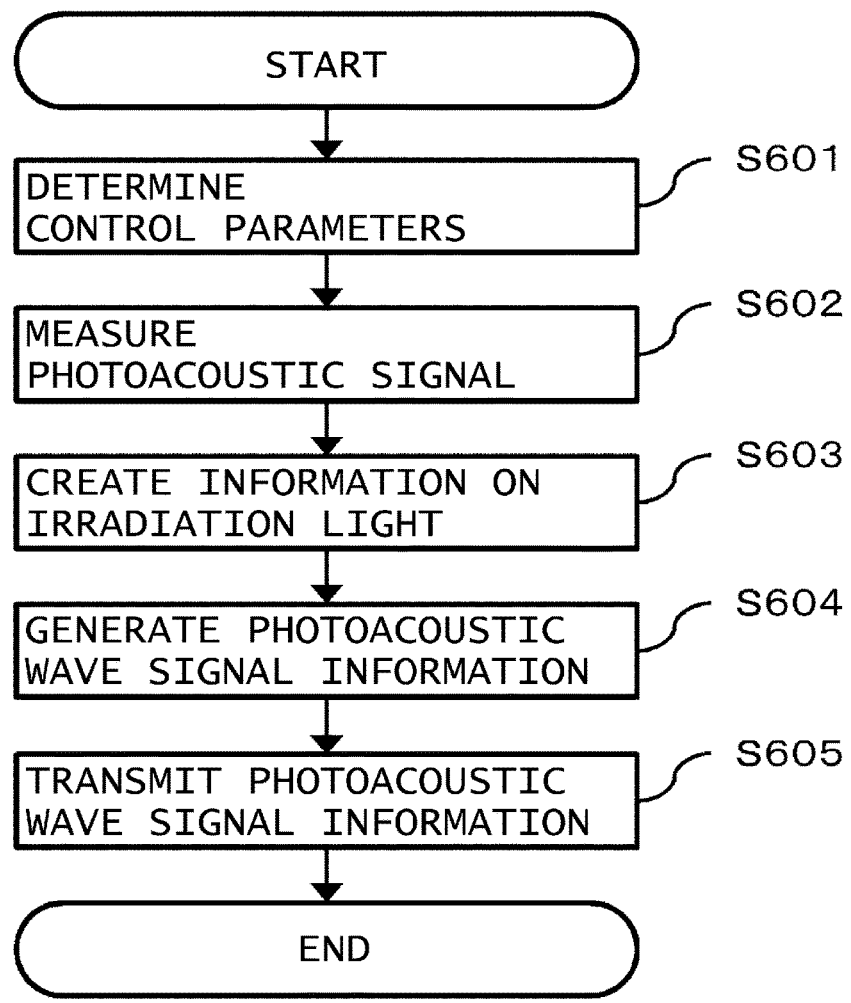
FIG. 6 is a flow chart depicting a processing procedure to acquire a photoacoustic wave signal.
Figure 7:
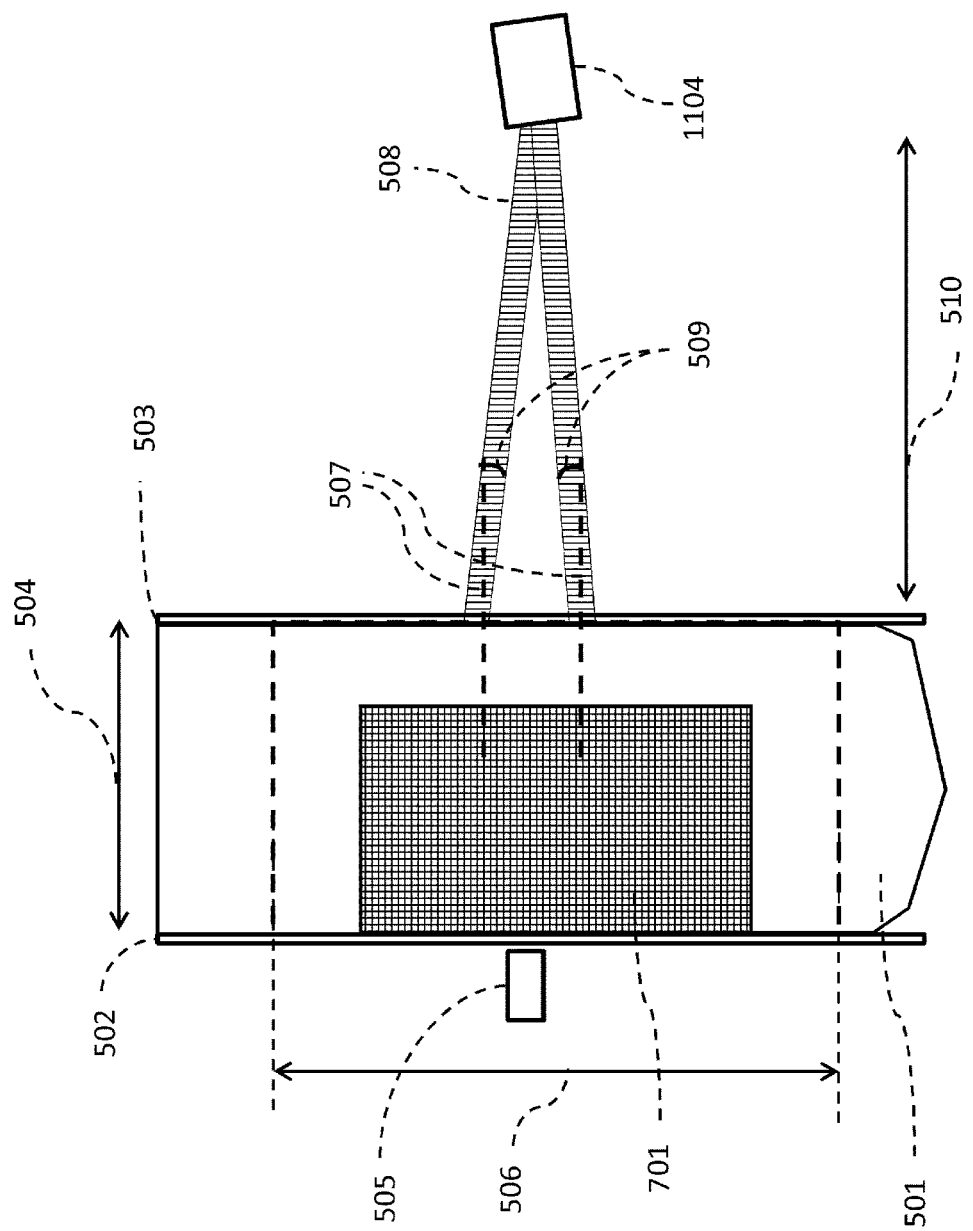
FIG. 7 is a diagram depicting a relationship between an object, a small imaging region and irradiated light.

FIG. 6 is a flow chart depicting the processing procedure when the photoacoustic wave measuring unit 1100 executes photoacoustic wave measurement, generates photoacoustic wave signal information, and transmits the photoacoustic wave signal information to the information processing unit 1000. This flow starts with the information processing unit 1000 receiving the acoustic wave measurement instruction information transmitted from the photoacoustic wave measurement method instructing unit 1004 of the information processing unit 1000.

In step S601, the photoacoustic wave signal measuring unit 1100 determines the control parameters to control the optical apparatus 1104 and the acoustic wave detector 1105. Examples of the control parameters are each irradiation position in the imaging region, the number of times of irradiation to a same position, irradiation timing, wave length and intensity (or density distribution). If a plurality of laser beams can be used, the control parameters of the irradiation light, such as type of laser beam, are determined. For the control of the acoustic wave detector 1105, control parameters for detecting a photoacoustic wave, such as a position of the probe, timing of the acoustic wave measurement and time, are determined. Control of the photoacoustic wave measurement and determination of control parameters are executed by the control unit 1102 based on the acoustic wave instruction information transmitted from the information processing unit 1000.

In step S602, the control unit 1102 detects an acoustic wave while synchronizing the photo-irradiation position and the probe position, and records data that is required for reconstructing the imaging region.

In step S603, information on the irradiation light to the imaging region is generated. This information includes both apparatus-specific information on the irradiation light which is converted so that this information can be handled relative to the imaging region, and information on the irradiation light which need not be converted. For irradiation position, direction and irradiation region of the light, position information on the coordinate system of the imaging region is generated.

If the irradiation light is diffused light, the size of the irradiation region changes as the distance 510 changes. For example, the focused spot radius of a Gaussian beam is normally given by Expression (8). This indicates that if a distance from the light emitting spot changes, the relative position with the beam waist (focal distance) changes, and the irradiation region size changes accordingly.

$$W = \lambda f / \pi W_0 \tag{8}$$

where W is a spot diameter, $W_0$ is an incident light radius, $\lambda$ is a wavelength, and f is a focal distance.

The size of the irradiation region can be measured using the reflection on the boundary surface of the imaging region, for example. The distance 510 and the size of the irradiation region may be provided in advance as a data table for each apparatus.

The incident angle of each irradiation light (angle formed by the optical axis and the normal line 507) is also generated on the coordinate system of the imaging region. For the light intensity, not the intensity at irradiation, but the intensity after the light transmitted through the holding plate 503 and decayed, is recorded as the intensity value or light density distribution. This information on the angle and intensity are included in the information on the irradiation light to the imaging region, and stored for each irradiation light. Information that is not different for each irradiation light, such as information on the wavelength and type of laser and the number of times of irradiation at a same position, are also stored together.

In this embodiment, information on the irradiation light is generated after the acoustic wave is measured, but the irradiation light information for the imaging region may be generated each time light is irradiated. In this case, the processing in step S602 and the processing in step S603 are repeated each time light is irradiated for measuring an acoustic wave. If a measuring apparatus, such as an optical sensor, is used, the intensity and incident angle of the irradiation light that reached the imaging region can be accurately measured.

In FIG. 5, the boundary surface of the imaging region (or reconstruction region) matches with the surface of the holding plate. Therefore the light that enters the imaging region is appropriately unchanged irradiation light, even if slight refraction or the like is generated by the holding plate. However if the imaging region (or reconstruction region) exists inside the object, as in the case of reference numeral 701 in FIG. 7, the light intensity distribution factor must be determined by estimating the light energy distribution, considering scattering and absorption. In this case, Expression (9), to determine the energy distribution of Gaussian scattering, for example, can be used. Then as information on the irradiation light to the imaging region, luminous flux, when the boundary surface of the imaging region is the cross-section, is calculated at each position of the boundary surface of the imaging region, based on the calculated light energy distribution.

$$P(\theta) = P_0 \exp[(-1/2) \cdot (\theta/\sigma)^2] \tag{9}$$

where $P(\theta)$ is a luminous intensity or radiance in the $\theta$ direction, $P_0$ is luminous intensity or radiance in a specular direction, and $\sigma$ is a standard deviation of Gaussian distribution.

When measurement of the acoustic wave ends, the control unit 1102 generates photoacoustic wave signal information in step S604. The photoacoustic wave signal information is information on an acoustic wave signal which the probe detected at each position on the scanning surface 502, and information on the irradiated light. If an acoustic wave signal is detected a plurality of times at a same position, a mean value or a representative value may be used. The information on the acoustic wave signal includes information on acoustic wave acquiring conditions for detecting an acoustic wave signal, or for determining an acoustic wave signal value.

In step S605, the photoacoustic wave signal measuring unit 1100 transmits the generated photoacoustic wave signal information to the information processing unit 1000.

By the above mentioned procedure, the acoustic wave acquiring unit 1100 measures the acoustic wave, and transmits the photoacoustic wave signal information to the information processing unit 1000.

Figure 8:
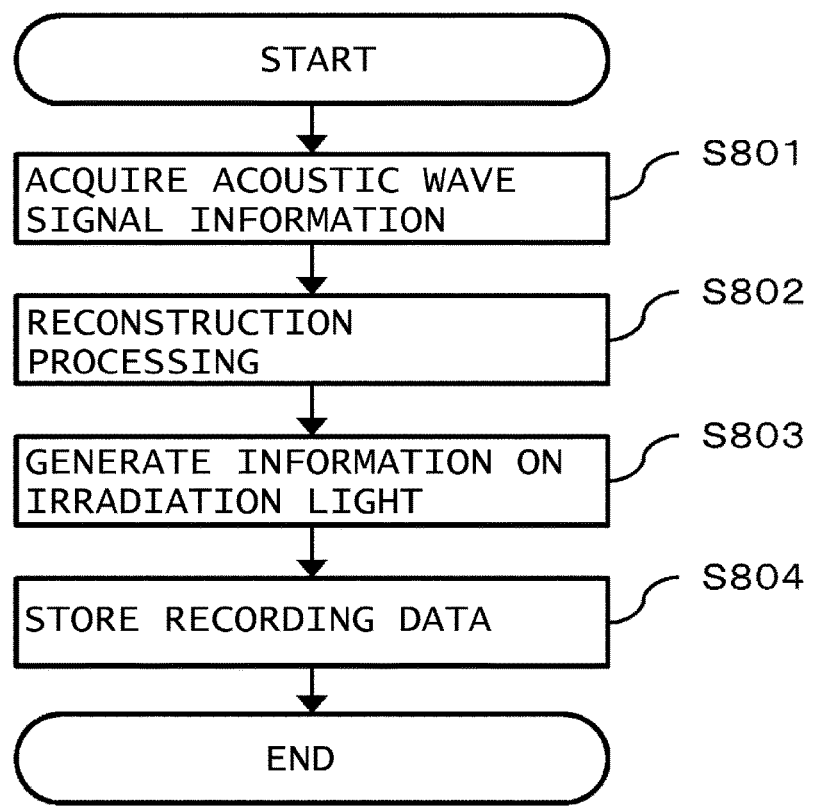
FIG. 8 is a flow chart depicting a procedure to convert and store information on an irradiated light.

FIG. 8 is a flow chart depicting a procedure when the information processing unit 1000 executes the reconstruction processing based on the photoacoustic wave signal information transmitted from the photoacoustic wave signal measuring unit 1100, and stores the recording data. The flow chart in FIG. 8 starts with the photoacoustic wave signal information acquiring unit 1005 receiving the photoacoustic wave signal information from the photoacoustic wave signal measuring unit 1100.

In step S801, the photoacoustic wave signal information acquiring unit 1005 transmits the acquired photoacoustic wave signal information to the reconstruction processing unit 1006 and the data generating unit 1007. Only the information on the irradiation light to the imaging region may be extracted and transmitted to the data generating unit 1007.

In step S802, the reconstruction processing unit 1006 performs reconstruction processing based on the received photoacoustic wave signal information, and information on the reconstruction method and the reconstruction region transmitted from the reconstruction method determining unit 1002, and generates the reconstructed image data of the imaging region. The reconstructed image data is generated, for example, as volume data that corresponds to the position and size of the imaging region. The reconstruction processing unit 1006 transmits the reconstructed image data to the data generating unit 1007.

In step S803, the data generating unit 1007 generates information on the irradiation light to the reconstructed image data, associating the reconstructed image data acquired from the reconstruction processing unit 1006 and the information on the irradiation light to the imaging region. To generate the recording data, DICOM image data, for example, is generated, and information on the irradiation light is checked and recorded in private tags. RAW data of the reconstructed image may be generated in an arbitrary format, with associating the size, type information or the like of this RAW data.

When information on the irradiation light for the reconstructed image data is generated, such information as the position of the irradiation light on the irradiation surface and the incident angle of the irradiation light is converted into coordinates in the voxel space of the volume data. Then the result is converted into a format that can be easily applied to the volume data. For example, if information on the irradiation light is too detailed compared with the pitch of the voxel of the volume data, the information is converted into a level matching the pitch of the voxel.

Figure 9:
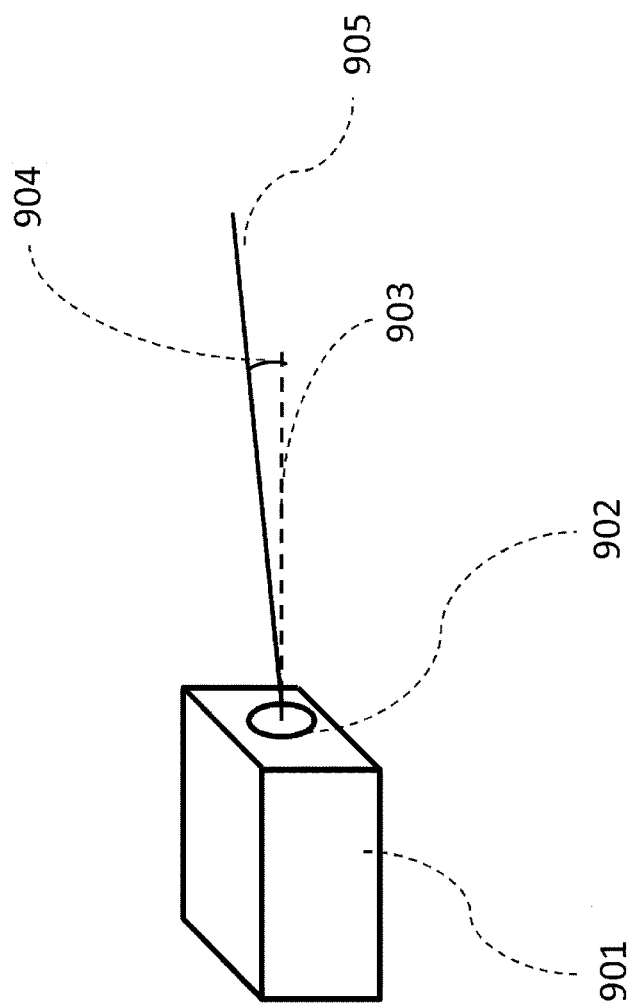
FIG. 9 is a diagram depicting an irradiated light for a small reconstruction region.

Now the positional relationship of the information on the irradiation light with respect to the reconstructed image data will be described with reference to a plurality of examples. FIG. 9 is a case when the imaging region is small, and the photo-irradiation position is only one location on the irradiation surface 902. The reference numeral 901 denotes volume data, the reference numeral 902 denotes an irradiation surface of light, the reference numeral 903 denotes a normal line, the reference numeral 904 denotes an incident angle θ, and the reference numeral 905 denotes an optical axis of the irradiation light. In this case, information on the irradiation light for the reconstructed image data is information on the irradiation light to one irradiation position. If the irradiation light is emitted to a same position for a plurality of times, information for each irradiation light may be stored, or a mean value may be stored.

Figure 10:
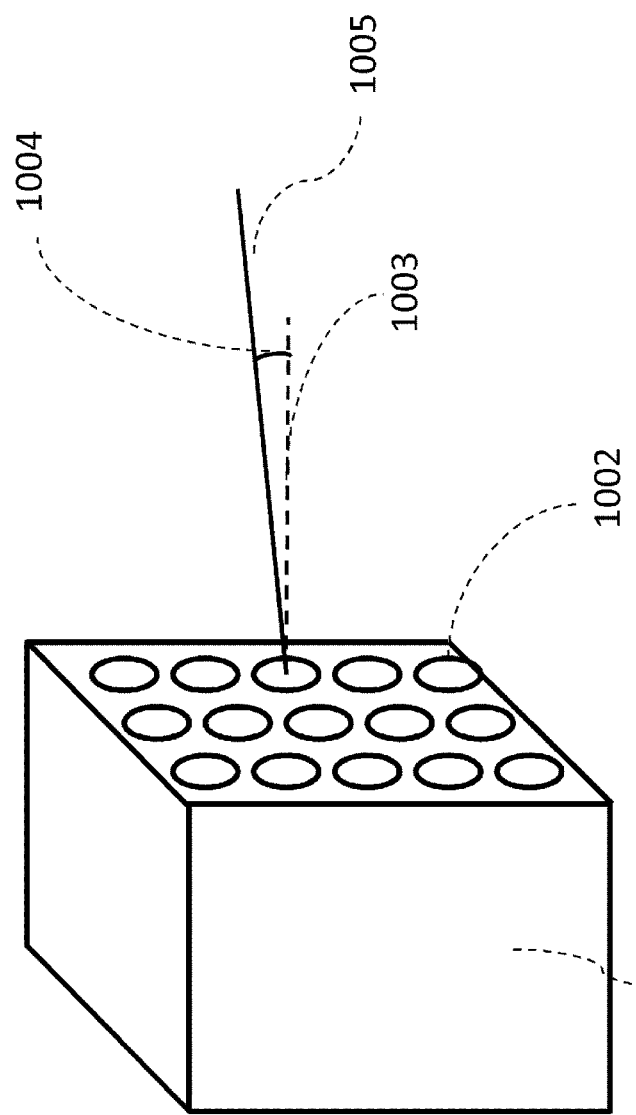
FIG. 10 is a diagram depicting an irradiated light for a large reconstruction region.

FIG. 10 is a case when the imaging region is large, and the photo-irradiation position exists on a plurality of irradiation surfaces 1002. The reference numeral 1001 denotes volume data, the reference numeral 1002 denotes an irradiation surface of the light, the reference numeral 1003 denotes a normal line, the reference numeral 1004 denotes an incident angle θ, and the reference numeral 1005 denotes an optical axis of the irradiation light. This corresponds to a case of acquiring an acoustic wave at each location during movement, while scanning the probe and the photo-irradiation position. In this case, information on a plurality of irradiation lights is generated for the volume data, and incident angle, intensity and shape of the irradiation surface are individually recorded for each irradiation light.

If the space between the actual photo-irradiation positions is small enough for the reconstructed image processing, information on the irradiation light may be simplified when the recording data is generated. For example, when reconstruction is possible only if the irradiated boundary surface of the volume data and the general irradiation direction are known, the information can be simplified.

Figure 11:
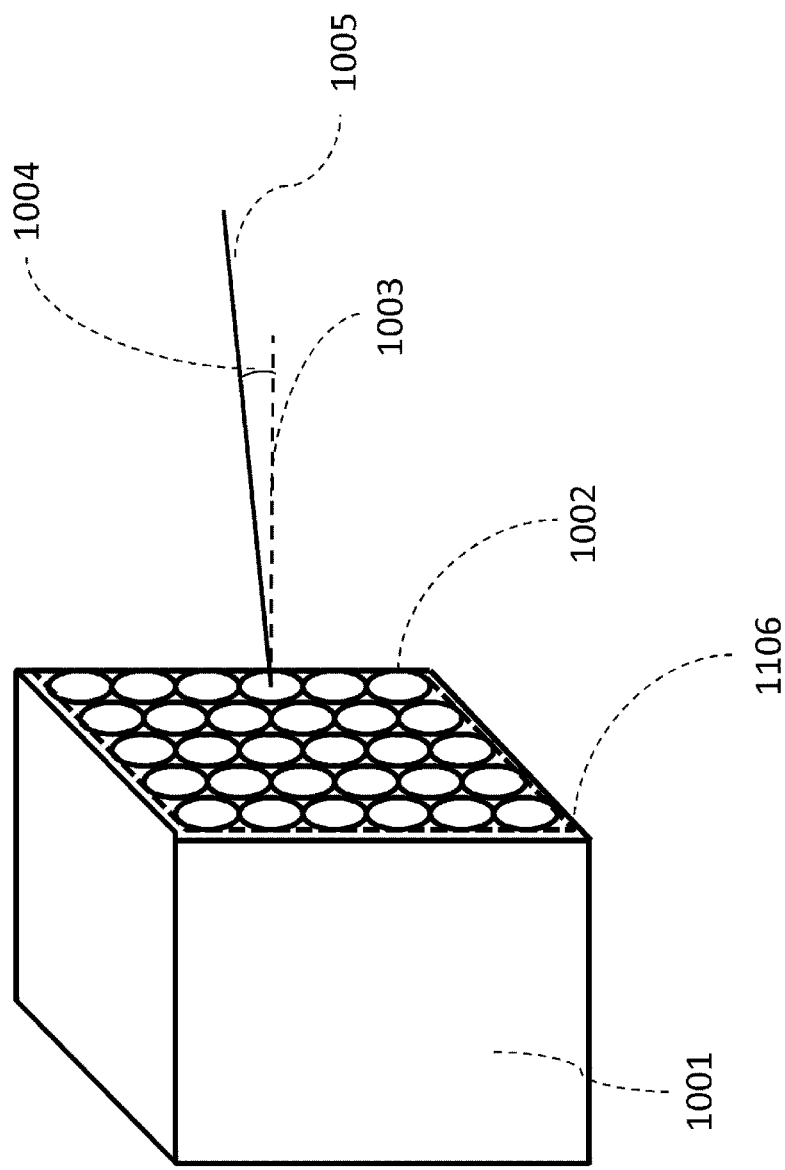
FIG. 11 is a diagram depicting simplified information on an irradiated light for a reconstruction region.

FIG. 11 shows an example of combined irradiation surfaces. The reference numerals 1001 to 1005 are the same as FIG. 10. The combined region 1106 of the irradiation surface is a region when the plurality of irradiation surfaces 1002, which corresponds to the plurality of photo-irradiation positions, is combined. This region is the boundary surface on the coordinate system of the volume data. Based on the intensity and incident angle of each irradiation light, one representative value (e.g. mean value) is generated and used as data on the irradiation light to the reconstructed image.

If such processing as averaging and simplification is performed when information on the irradiation light to the imaging region is converted into information on the irradiation light to the reconstructed image, an identifier of the type of information on the irradiation light to the reconstructed image is also included in the recording data.

In FIG. 11, the irradiation light is irradiated only to one boundary surface, but may be irradiated onto a plurality of boundary surfaces. For example, if light is also irradiated from the opposite side of the object simultaneously, light intensity in the imaging region increases, and an image with high contrast can be acquired.

The data generating unit 1007 transmits the recording data, in which the reconstructed image data and information on the irradiation light to the reconstructed image are recorded, to the data recording unit 1008.

In step S804, the data recording unit 1008 stores the recording data generated by the data generating unit 1007 to a storage medium.

Figure 12:
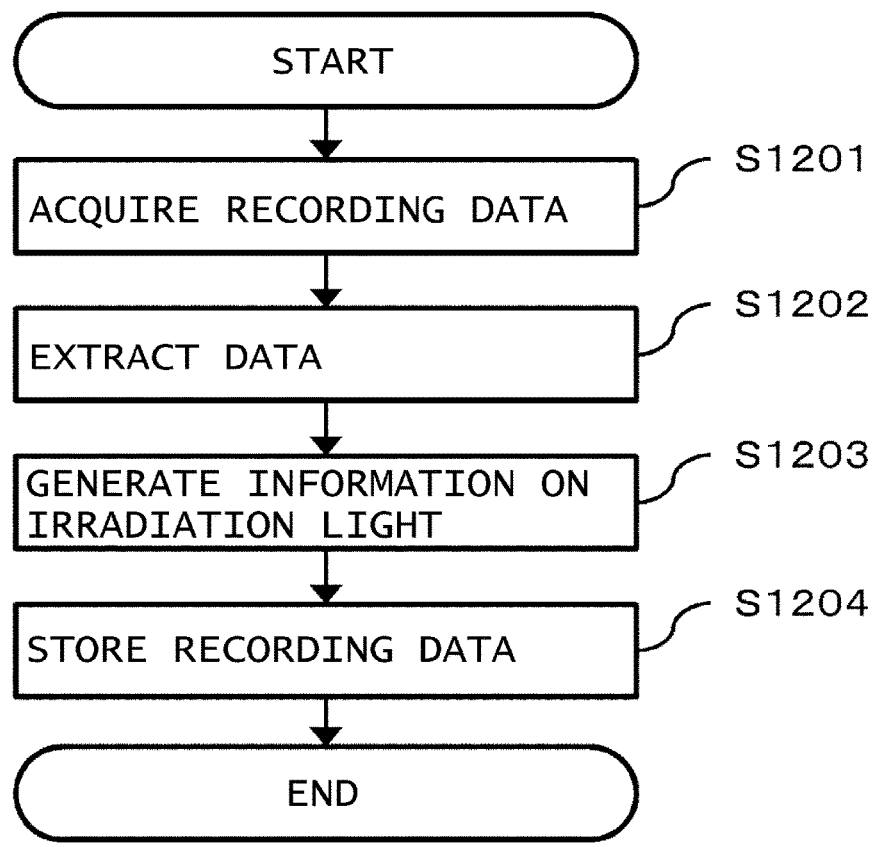
FIG. 12 is a flow chart depicting a procedure to use information on the stored irradiated light.

A procedure to display a reconstructed image using information on the irradiation light stored in the recording data will be described with reference to the flow chart in FIG. 12. The flow chart in FIG. 12 starts with the information processing unit 1000 reading the recording data from the recording data file 1200.

In step S1201, the data acquiring unit 1009 reads the recording data from the recording data file 1200, and transmits the recording data to the data analyzing unit 1010.

In step S1202, the data analyzing unit 1010 extracts the reconstructed image data and the information on the irradiation light to the reconstructed image, including an identifier of the type of the information from the recording data, and transmits the extracted information to the display information generating unit 1011.

The display information generating unit 1011 generates display image information of the reconstructed image that can be displayed on the display unit 1012, using the reconstructed image data. For example, if the reconstructed image is displayed by MPR (Multi-Planar Reconstruction), the cross-sectional image of the reconstructed image and the boundary line of the region divided based on the quality of the image are superposed and displayed. An image acquired by volume rending can also be displayed. Color and graphics may be added so that the irradiated boundary surface of the reconstructed image is distinguished from the other boundary surfaces, and the influence of the light can be recognized more easily.

Graphics to be added to the display image may be changed depending on the type of the information on the irradiation light. For example, if information on the irradiation light is simplified, an arrow mark indicating the direction of the light may be added, and if the information on the irradiation light is provided for each irradiation position, information on the shape of the irradiation surface and the optical axis may be added for each position. If the intensity of the irradiation light is displayed as color-coded depending on the level, the relationship of the color and intensity can be displayed by a graph or color bar. Furthermore, information other than an image, such as description using text, based on a pixel value of each position of a three-dimensional reconstructed image, that is a voxel value of volume data, may be displayed.

Further, the quality of decay, intensity or the like of the light in the reconstructed image may be understood and displayed. Such information can be estimated by a shape and size of the irradiation surface, an incidence angle, an intensity value (or light density), a wavelength, a scattering coefficient of the object among other factors. Thereby the user can understand a region where the intensity of the irradiation light is sufficient and a region where this intensity is not sufficient, and the difference of image quality can be recognized.

If volume rendering is performed, it becomes difficult for the user to understand a region where image quality is different, because the image is rotated three-dimensionally, and apparatus information during the imaging process is lost. In such a case, display image information, where graphics and annotation are added to make it easier to recognize a region influenced by the irradiation light for the reconstructed image, can be easily attached without recording or analyzing redundant data that depends on the imaging apparatus.

If a region in the object which interrupts propagation or scattering of light can be determined based on the distribution of the light absorption coefficients in the reconstructed image, this information may be displayed. For example, a region where the shadow of the irradiation light is generated in the reconstructed image or a region where the scattering of the light is not uniform can be displayed. If the information can be used as an input value for calculating other analysis data, like the case of calculating oxygen saturation from the reconstructed image to indicate the initial sound pressure distribution of a photoacoustic wave, the accuracy of the analysis result improves by considering the quality of the conditions of the irradiation light in the reconstructed image using the information on the irradiation light.

The display information generating unit 1011 transmits the generated display information to the display unit 1012. The display unit 1012 displays the received display information. By the procedure described above, the recording data is read and the reconstructed image can be displayed using the stored information on the irradiation light.

In this embodiment, the photoacoustic wave signal measuring unit 1100 generates the information on the irradiation light to the imaging region, and the information processing unit 1000 generates information on the irradiation light to the reconstructed image. However the photoacoustic wave signal measuring unit 1100 may generate information on the reconstruction region. The information processing unit 1000, rather than the photoacoustic wave signal measuring unit 1100, may generate the information on the irradiation light to the imaging region. The data generating unit 1009 may perform the calculation on scattering of the transmitted light inside the object.

The photoacoustic wave measurement method determining unit 1003 may be integrated with the photoacoustic wave measuring unit 1100. Further, an imaging apparatus in which the information processing unit 1000 and the photoacoustic wave signal measuring unit 1100 are integrated may be used. The information processing unit 1000 comprising only the data acquiring unit 1009, the data analyzing unit 1010, the display information generating unit 1011 and the display unit 1012, out of the above mentioned components of the information processing unit 1000, may access the recording data file 1200.

According to the apparatus configuration and procedure described above, display image information considering the influence of the light in the reconstructed image, and recording data that can be used for calculating the analysis result can be provided without using a special format, and without the cost of using an enormous amount of apparatus-specific data. Furthermore, standard volume data can be acquired, therefore a standard viewer and analysis software can be used, and recording data which is less restricted by application can be generated and used.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2012-158988, filed on Jul. 17, 2012, which is hereby incorporated by reference herein in its entirety.

The invention claimed is:

1. An object information acquiring apparatus comprising:
at least one CPU; and
memory,
wherein said at least one CPU and said memory cooperate to function as:
a processing unit configured to generate a DICOM image representing characteristic information on an object based on an acoustic wave generated from the object which has received irradiation light;
a data generating unit configured to generate, in a DICOM data format, a recording data by storing information of the irradiation light in a tag and attaching the tag to the DICOM image representing the characteristic information and configured to transmit the recording data to a data recording unit configured to record the recording data.

2. The object information acquiring apparatus according to claim 1, wherein said processing unit segments the object into a plurality of unit regions, and generates the DICOM image representing characteristic information for each unit region, and
said data generating unit generates the recording data by storing the information of the irradiation light in the tag and attaching the tag to the DICOM image representing the characteristic information for each unit region.

3. The object information acquiring apparatus according to claim 1, wherein the information of the irradiation light includes information of an angle of the irradiation light with respect to the object.

4. The object information acquiring apparatus according to claim 1, wherein the information of the irradiation light includes information of wavelength of the irradiation light.

5. The object information acquiring apparatus according to claim 1, wherein the information of the irradiation light includes information of a number of times photo-irradiation is executed.

6. The object information acquiring apparatus according to claim 2, wherein said processing unit determines information on an image quality in each of the unit regions based on the information of the irradiation light included in the recording data and causes a display unit to display the DICOM image with the information on the image quality.

7. An object information acquiring method comprising:
a step of generating a DICOM image representing characteristic information on an object based on an acoustic wave generated from the object which has received irradiation light;
a step of generating, in a DICOM data format, a recording data by storing information of the irradiation light in a tag and attaching the tag to the DICOM image representing the characteristic information; and
a step of transmitting the recording data to a data recording unit configured to record the recording data,
said steps being performed by at least a CPU and memory acting in cooperation to perform said steps.

8. The object information acquiring apparatus according to claim 1, wherein said processing unit is configured to generate the DICOM image representing the characteristic information in a reconstruction region,
said data generating unit generates the recording data by storing the information of the irradiation light at a boundary surface of the reconstruction region in the tag and attaching the tag to the DICOM image representing the characteristic information in the reconstruction region, and said processing unit reads the recording data from the data recording unit and causes a display unit to display the DICOM image with the information of the irradiation light at the boundary surface of the reconstruction region.

9. The object information acquiring apparatus according to claim 3, wherein said processing unit causes a display unit to display the DICOM image with a line to represent an optical axis corresponding to the angle of the irradiation light based on the recording data.

10. The object information acquiring apparatus according to claim 1, wherein the information of the irradiation light includes an intensity of the irradiation light in the object, and wherein said processing unit causes a display unit to display the DICOM image with color-coding depending on the intensity of the irradiation light based on the recording data.

11. The object information acquiring apparatus according to claim 1, wherein said processing unit causes a display unit to display the DICOM image representing characteristic information on the object with the information of the irradiation light based on the recording data.

12. The object information acquiring method according to claim 9, further comprising:
a step of displaying the DICOM image representing characteristic information on the object with the information of the irradiation light based on the recording data.

13. The object information acquiring apparatus according to claim 1, wherein said data generating unit transmits the recording data to an external data recording unit as the data recording unit via a network.

14. The object information acquiring apparatus according to claim 1, further comprising:
a light source; and
an acoustic wave detector comprising at least one detection element, configured to detect the acoustic wave generated by irradiating the object with irradiation light from said light source and output a signal,
wherein said processing unit generates the DICOM image representing the characteristic information by using the signal output from said acoustic wave detector.

15. The object information acquiring method according to claim 9, further comprising:
a step of segmenting the object into a plurality of unit regions, wherein the DICOM image representing the characteristic information for each unit region is generated, and
the recording data is generated by storing the information of the irradiation light in the tag and attaching the tag to the DICOM image representing the characteristic information for each unit region.

16. The object information acquiring method according to claim 15, further comprising:
a step of determining information on an image quality in each of the unit regions based on the information of the irradiation light included in the recording data, and
a step of displaying the DICOM image with the information on the image quality.

17. The object information acquiring method according to claim 9, further comprising:
a step of displaying the information of the irradiation light,
wherein the DICOM image representing the characteristic information in a reconstruction region is generated,
the recording data is generated by storing the information of the irradiation light at a boundary surface of the reconstruction region in the tag and attaching the tag to the DICOM image representing the characteristic information in the reconstruction region, and
the information of the irradiation light at the boundary surface of the reconstruction region is displayed based on the recording data.

18. The object information acquiring method according to claim 9, further comprising:
a step of displaying the DICOM image with a line to represent an optical axis corresponding to an angle of the irradiation light based on the recording data, the information of the irradiation light including information of the angle of the irradiation light with respect to the object.

19. The object information acquiring method according to claim 9, further comprising:
a step of displaying the DICOM image with color-coding depending on an intensity of the irradiation light in the object based on the recording data, the information of the irradiation light including the intensity of the irradiation light in the object.

20. The object information acquiring method according to claim 9, wherein the recording data is transmitted to an external data recording unit as the data recording unit via a network.

21. The object information acquiring method according to claim 9, wherein the information of the irradiation light includes information of an angle of the irradiation light with respect to the object.

22. The object information acquiring method according to claim 9, wherein the information of the irradiation light includes information of wavelength of the irradiation light.

23. The object information acquiring method according to claim 9, wherein the information of the irradiation light includes information of a number of times photo-irradiation is executed.

* * * * *